(12) United States Patent
Zanger

(10) Patent No.: US 6,303,630 B1
(45) Date of Patent: *Oct. 16, 2001

(54) DIARYLSULFONE NON-NUCLEOSIDE REVERSE TRANSCRIPTASE INHIBITORS OF HUMAN IMMUNODEFICIENCY VIRUS

(75) Inventor: Murray Zanger, Havertown, PA (US)

(73) Assignee: University of the Sciences in Philadelphia, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/547,820

(22) Filed: Apr. 11, 2000

Related U.S. Application Data

(63) Continuation of application No. 08/901,919, filed on Jul. 29, 1997, now Pat. No. 6,063,790.

(51) Int. Cl.$^7$ .................... A61K 31/47; A61K 31/10; A61K 31/136; A61P 31/18; C07D 215/36; C07C 317/14

(52) U.S. Cl. .................... 514/311; 514/312; 514/603; 514/709; 546/153; 546/166; 564/87; 568/30; 568/33; 568/34

(58) Field of Search .................... 546/153, 166; 564/87; 568/30, 33, 34; 514/311, 312, 603, 709

(56) References Cited

U.S. PATENT DOCUMENTS

| | | | |
|---|---|---|---|
| 4,505,929 | 3/1985 | Markley et al. | 514/520 |
| 5,017,610 * | 5/1991 | Imaki | 514/546 |
| 5,278,173 | 1/1994 | Davis | 514/312 |
| 5,308,854 | 5/1994 | Hoffman, Jr. et al. | 514/338 |
| 5,444,036 * | 8/1995 | Iwasaki | 503/209 |
| 5,545,750 | 8/1996 | Kempf et al. | 564/360 |
| 5,565,200 | 10/1996 | Khwaja | 424/195.1 |
| 5,679,695 * | 10/1997 | Wassmundt | 514/347 |

FOREIGN PATENT DOCUMENTS

| | | | |
|---|---|---|---|
| 347168 * | 12/1989 | (EP) | . |
| 475707 * | 3/1992 | (EP) | . |
| 610653 * | 8/1994 | (EP) | . |
| 57167465 * | 10/1982 | (JP) | . |
| 61003780 * | 1/1986 | (JP) | . |
| 9206683 * | 4/1992 | (WO) | . |
| 6804213 * | 1/1969 | (ZA) | . |

OTHER PUBLICATIONS

Kuboyama K et al. Bunseki Kagaku, 45(1), 71–6, 1996.*
Chechegoeva EV et al. Zh. Org. Khim., 2 (7), 1321, 1966.*
Burmistrov SI et al. Ukr. Khim. Zh., 33(2), 183–4, 1967.*
Litvinenko LM et al. Zh. Obshch. Khim., 40 (4) 886–94, 1970.*
Sheiko SG et al. Zh. Org. Khim., 14 (12), 2565–9, 1978.*
Buckheit RW et al. Antiviral Chem. Chemother., 7(5), 243–252, 1996.*
McMahon JB et al. Antimicrob. Agents Chemother., 37(4), 754–60, 1993.*
Gennaro AR et al. J. Org. Chem., 36(9), 1321–4, 1971.*
Artico et al., "Synthesis of Pyrryl Aryl Sulfones Targeted at the HIV–1 Reverse Transcriptase", Arch. Pharm. vol. 328, pp. 223–229 (1995) (Weinheim).

* cited by examiner

*Primary Examiner*—Evelyn Mei Huang
(74) *Attorney, Agent, or Firm*—Duane Morris & Heckscher LLP

(57) ABSTRACT

In accordance with the present invention, there is now provided novel anti-HIV compounds of the formulae selected from the group consisting of:

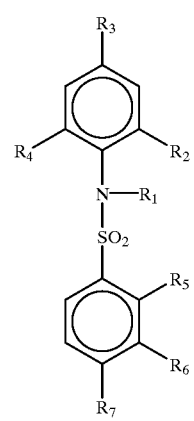

(I)

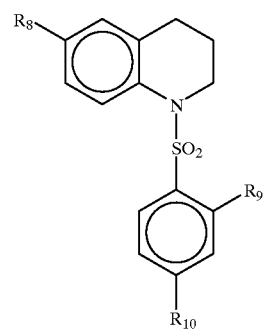

(II)

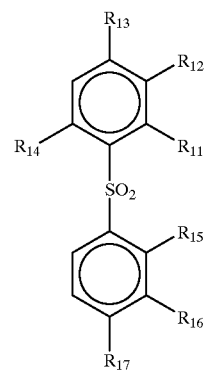

(III)

-continued

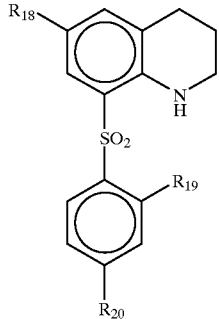

(IV)

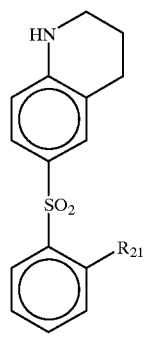

(V)

wherein $R_1$ is hydrogen or $C_1$–$C_4$ alkyl; $R_2$ is hydrogen, $C_1$–$C_4$ alkyl, $C_1$–$C_4$ alkoxy or halogen; $R_3$ is hydrogen, hydroxy, $C_1$–$C_4$ alkyl, $C_1$–$C_4$ alkoxy or halogen; $R_4$ is hydrogen or halogen, $R_5$ is hydrogen; $C_1$–$C_4$ alkoxy, nitro, halogen or haloalkyl; $R_6$ is hydrogen or nitro; $R_7$ is hydrogen or $C_1$–$C_4$ alkyl, $C_1$–$C_4$ alkoxy, nitro or halogen; $R_8$ is hydrogen, hydroxy, $C_1$–$C_4$ alkyl, $C_1$–$C_4$ alkoxy or halogen; $R_9$ is hydrogen or nitro; $R_{10}$ is hydrogen or halogen; $R_{11}$ is hydrogen, $C_1$–$C_4$ amine; $R_{12}$ is hydrogen, $C_1$–$C_4$ alkyl or halogen; $R_{13}$ is hydrogen, $C_1$–$C_4$ amine; $R_{14}$ is hydrogen or halogen; $R_{15}$ is hydrogen, $C_1$–$C_4$ alkoxy, $C_1$–$C_4$ haloalkyl, nitro, or halogen; $R_{16}$ is hydrogen or nitro; $R_{17}$ is hydrogen, $C_1$–$C_4$ alkyl, $C_1$–$C_4$ alkoxy, nitro or halogen; $R_{18}$ is hydrogen, $C_1$–$C_4$ alkoxy, hydroxy, or halogen; $R_{19}$ is hydrogen or nitro; and $R_{20}$ is hydrogen or halogen, or a pharmaceutically acceptable salt thereof.

3 Claims, No Drawings

US 6,303,630 B1

DIARYLSULFONE NON-NUCLEOSIDE REVERSE TRANSCRIPTASE INHIBITORS OF HUMAN IMMUNODEFICIENCY VIRUS

This application is the continuation of U.S. patent application 08/901,919, filed on Jul. 29, 1997, now U.S. Pat. No. 6,063,790.

FIELD OF THE INVENTION

The present invention relates to diarylsulfones, substituted diarylsulfones and related derivatives which possess anti-immunodeficiency virus efficacy.

BACKGROUND OF THE INVENTION

Diarylsulfones are known chemotherapeutic agents which are a new class of non-nucleoside reverse transcriptase inhibitors with various structural features responsible for their antiviral activity having been identified.

Variously substituted diaryl sulfones and related derivatives showing activity against immunodeficiency virus (HIV) have been reported in McMahon et al., *Antimicrobial Agents and Chemotherapy*, 37(4): 754–760 (1993), "Diarylsulfones, A New Chemical Class of Nonnucleoside Antiviral Inhibitors of Human Immunodeficiency Antiviral inhibitors of Human Immunodeficiency Virus Type 1 Reverse Transcriptase". In the reference, substituted diaryl sulfones and related derivatives were found to specifically prevent HIV Type 1 (HIV-1) replication and HIV-1 induced cell killing in vitro. As reported in McMahon et al., 2-nitrophenyl phenylsulfone was found to display high efficacy in protecting human cells in culture from HIV-1 cytopathic effects, as well as inhibition of HIV-1 replication via inhibition of HIV-1 reverse transcriptase. The base structure for compounds tested for biological activity in this reference is as follows:

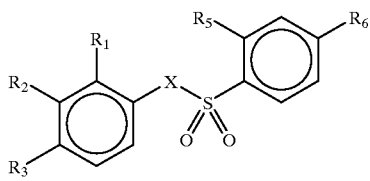

Buckheit et al., *Antiviral Chemistry & Chemotherapy* 7 (5): 243–252 (1996) reports structure-activity relationship evaluations with several diarylsulfone non-nucleoside reverse transcriptase inhibitors. As set forth in this reference, it was observed that steric properties of various molecules and compound lipophilicity contributed to compound biological activity against HIV-1, with the most active compounds being diarylsulfones having an orthonitro group yielding anti-HIV-1 activity at sub-micromolar concentrations. Further, diarylsulfone compounds were found to exhibit antiviral properties in a manner similar to other members of the class of HIV-1 specific reverse transcriptase inhibitors, as well as synergistic inhibitors of HIV-1 by certain diarylsulfone compounds used in combination with nucleoside analogues AZT, ddI, 3TC, d4T, and protease inhibitor KN1-272.

In Antico et al., *Arch. Pharm.* (Weinheim) 328, 223–229 (1995), several diarylsulfone compounds were found to be selectively active as anti-HIV-1 agents with the most efficacy shown by 2-nitrophenyl 1-pyrryl sulfone wizh a carbethoxy group at the 2 position of pyrrole. In fact, unlike 2-nitro-phenyl phenyl sulfone (NPPS), only derivatives bearing a carbethoxy group in the pyrrole ring 2 position were shown to exhibit anti-HIV-1 efficacy. Thus, as reported, in Artico et al., unlike the NPPS diarylsulfone structure,

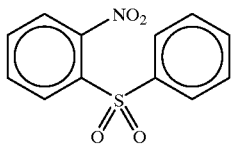

in order to act as an anti-HIV agent, the 2-nitrophenyl 1-pyrryl sulfone skeleton must have the presence of a carbethoxy functional group, such as,

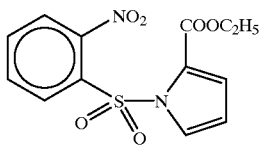

Other references which describe inhibition of HIV reverse transcriptase by sulfones are U.S. Pat. No. 5,308,854 (thiamorpholinyl sulfone) and U.S. Pat. No. 5,565,200 (divinyl sulfone) in which the sulfone group is not a linking group between aryl groups.

Further, U.S. Pat. No. 5,545,750 describes retroviral protease inhibiting compounds of the formula A-X-B, wherein X can be a sulfone linking group, and in which A and B can be functionalized, cyclic groups which are limited to heterocyclic groups. Bis-(2-phenyl ethyl) sulfone is also discussed in this reference U.S. Pat. No. 4,505,929 describes an anti-retroviral-exhibiting compound in which a sulfone group is a linking group between an "R" group which may be a phenyl group and a diphenyl ether group (a sulfone phenyl diphenyl ether).

Additionally, U.S. Pat. No. 5,278,173 discloses the use of diaminodiphenyl sulfone in inhibiting HIV activity in vivo.

SUMMARY OF THE INVENTION

In accordance with this invention, several novel anti-HIV compounds are now provided which have the formulae selected from the group consisting of:

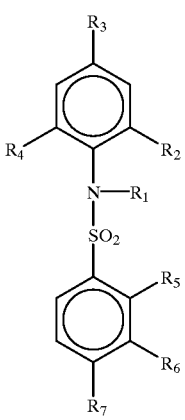

(I)

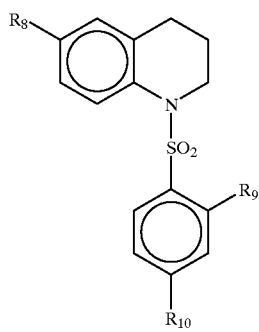

(II)

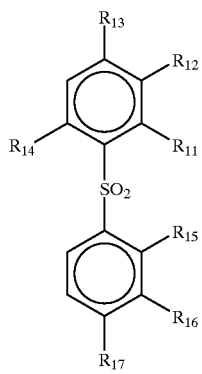

(III)

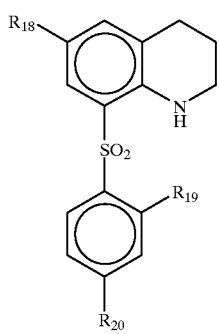

(IV)

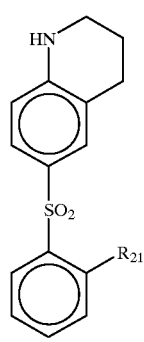

(V)

wherein $R_1$ is hydrogen or $C_1$–$C_4$ alkyl; $R_2$ is hydrogen, $C_1$–$C_4$ alkyl, $C_1$–$C_4$ alkoxy or halogen; $R_3$ is hydrogen, hydroxy, $C_1$–$C_4$ alkyl; $C_1$–$C_4$ alkoxy or halogen; $R_4$ is hydrogen or halogen; $R_5$ is hydrogen, $C_1$–$C_4$ alkoxy, nitro, halogen or haloalkyl; $R_6$ is hydrogen or nitro; $R_7$ is hydrogen, $C_1$–$C_4$ alkyl, $C_1$–$C_4$ alkoxy, nitro or halogen; $R_8$ is hydrogen, hydroxy, $C_1$–$C_4$ alkyl, $C_1$–$C_4$ alkoxy or halogen; $R_9$ is hydrogen or nitro; $R_{10}$ is hydrogen or halogen; $R_{11}$ is hydrogen, $C_1$–$C_4$ amine; $R_{12}$ is hydrogen, $C_1$–$C_4$ alkyl or halogen; $R_{13}$ is hydrogen, $C_1$–$C_4$ amine; $R_{14}$ is hydrogen or halogen; $R_{15}$ is hydrogen, $C_1$–$C_4$ alkoxy, $C_1$–$C_4$ haloalkyl, nitro, or halogen; $R_{16}$ is hydrogen or nitro; $R_{17}$ is hydrogen, $C_1$–$C_4$ alkyl, $C_1$–$C_4$ alkoxy, nitro or halogen; $R_{18}$ is hydrogen, $C_1$–$C_4$ alkoxy, hydroxy, or halogen; $R_{19}$ is hydrogen or nitro; and $R_{20}$ is hydrogen or halogen, or a pharmaceutically acceptable salt thereof.

In another aspect of the invention, it has been found that the aforesaid compounds which possess an octanol/water partition coefficient (logP) of from about 2.5 to about 4, are preferred in their display of anti-HIV efficacy.

The invention is more fully described with reference to the following detailed description of preferred embodiments and illustrative examples.

DETAILED DESCRIPTION OF PREFERRED EMBODIMENTS

As set forth hereinabove, the present invention provides a series of substituted and unsubstituted diaryl sulfone and diaryl sulfonamide compounds which have unexpectedly and surprisingly been shown to possess anti-HIV efficacy. The compounds of this invention have the following formula:

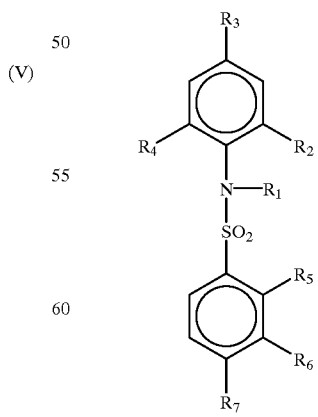

(I)

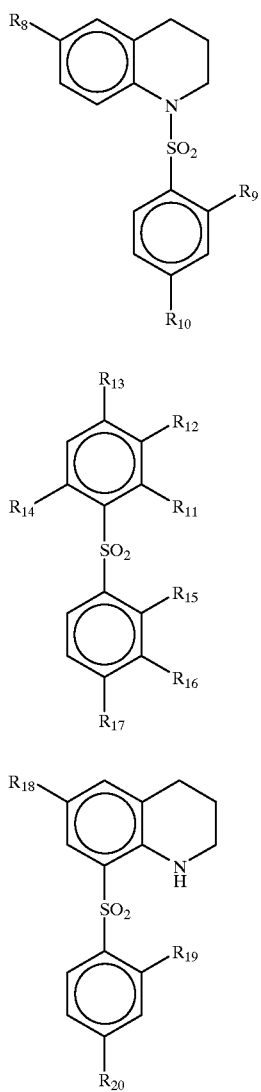

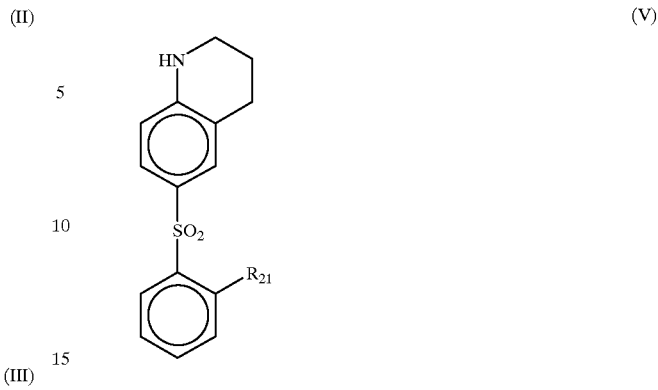

wherein $R_1$ is hydrogen or $C_1$–$C_4$ alkyl; $R_2$ is hydrogen, $C_1$–$C_4$ alkyl, $C_1$–$C_4$ alkoxy or halogen; $R_3$ is hydrogen, hydroxy, $C_1$–$C_4$ alkyl; $C_1$–$C_4$ alkoxy or halogen; $R_4$ is hydrogen or halogen; $R_5$ is hydrogen, $C_1$–$C_4$ alkoxy, nitro, halogen or haloalkyl; $R_6$ is hydrogen or nitro; $R_7$ is hydrogen, $C_1$–$C_4$ alkyl, $C_1$–$C_4$ alkoxy, nitro or halogen; $R_8$ is hydrogen, hydroxy, $C_1$–$C_4$ alkyl, $C_1$–$C_4$ alkoxy or halogen; $R_9$ is hydrogen or nitro; $R_{10}$ is hydrogen or halogen; $R_{11}$ is hydrogen, $C_1$–$C_4$ amine; $R_{12}$ is hydrogen, $C_1$–$C_4$ alkyl or halogen; $R_{13}$ is hydrogen, $C_1$–$C_4$ amine; $R_{14}$ is hydrogen or halogen; $R_{15}$ is hydrogen, $C_1$–$C_4$ alkoxy, $C_1$–$C_4$ haloalkyl, nitro, or halogen; $R_{16}$ is hydrogen or nitro; $R_{17}$ is hydrogen, $C_1$–$C_4$ alkyl, $C_1$–$C_4$ alkoxy, nitro or halogen; $R_{18}$ is hydrogen, $C_1$–$C_4$ alkoxy, hydroxy, or halogen; $R_{19}$ is hydrogen or nitro; and $R_{20}$ is hydrogen or halogen, or a pharmaceutically acceptable salt thereof.

The anti-HIV active diaryl sulfone compounds of the present invention can be prepared, for example, via acid catalyzed rearrangement of N-alkylbenzene sulfonanilides, as set forth, for example, in Khan, "Kinetics and Mechanism of the Acid-Catalyzed Rearrangement of N-Alkyl Arylsulfonanilides", Ph.D. Dissertation, Philadelphia College of Pharmacy (May 1975), as follows:

ROUTE A

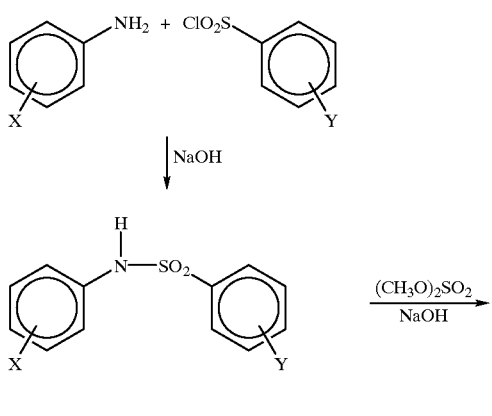

ROUTE B

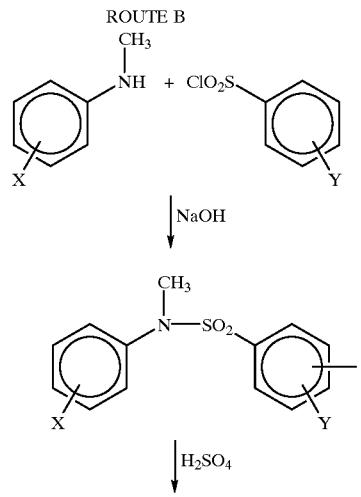

-continued

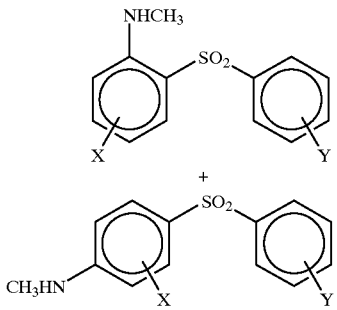

Substituted N-methylbenzene sulfonanilides with varying substituents on the aniline portion of the molecule as starting reagents in the preparation of compounds of this invention can be prepared by dissolving the appropriate amine in ethanol along with an equimolar amount of benzenesulfonyl chloride, and then allowing the mixture to react. To this mixture is added 10% sodium hydroxide dropwise with stirring until the solution is lightly alkaline. The precipitate of the corresponding benzenesulfonanilide is obtained upon cooling the reaction mixture. Next, the crude precipitate of the corresponding N-methyl-benzene-sulfonanilide is obtained upon cooling the mixture. Crude precipitates can be crystallized successively from ethanol and glacial acetic acid, with high purity being obtained. Table 1 below includes illustrative benzenesulfonanilides prepared as described above.

TABLE 1

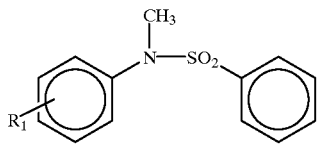

| Compound | $R_1$ | LogP |
|---|---|---|
| 1 | 4-OCH$_3$ | 3.15 |
| 2 | 4-Br | 4.06 |
| 3 | 4-Cl | 3.81 |
| 4 | 2-Cl | 3.81 |
| 5 | 4-Me | 3.66 |

N-alkylbenzenesulfonanilides with varying substituents on the benzene sulfonic acid portion of the molecule can be prepared by dissolving freshly distilled N-methylaniline or tetrahydroquinoline in ethanol, along with an equimolar amount of the appropriate sulfonyl chloride dissolved in ethanol, and stirring the reaction mixture well. Precipitate is obtained upon addition of ten percent sodium hydroxide solution, and crude precipitate is crystallized using ethanol and/or acetic acid. Table 2 below illustrates some of the various compounds that can be prepared using this method.

TABLE 2

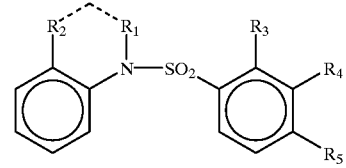

| Compound | $R_1$ | $R_2$ | $R_3$ | $R_4$ | $R_5$ | lopP |
|---|---|---|---|---|---|---|
| 6 | —(CH$_2$)$_3$— | | H | H | H | 4.05 |
| 7 | —(CH$_2$)$_3$— | | NO$_2$ | H | H | 3.91 |
| 8 | Me | H | H | H | H | 3.19 |
| 9 | Me | H | H | H | OMe | 3.15 |
| 10 | Me | H | H | H | Br | 4.06 |
| 11 | Me | H | H | H | Cl | 3.81 |
| 12 | Me | H | H | H | Me | 3.66 |
| 13 | Me | H | NO$_2$ | H | H | 3.09 |
| 14 | Me | H | H | NO$_2$ | H | 3.09 |
| 15 | Me | H | H | H | NO$_2$ | 3.09 |
| 16 | Et | H | NO$_2$ | H | H | 3.82 |
| 17 | Me | H | Cl | H | H | 3.81 |
| 18 | Me | H | Br | H | H | 4.06 |
| 19 | Me | H | CF$_3$ | H | H | 4.18 |
| 20 | Me | H | OMe | H | Cl | 3.76 |
| 21 | Me | H | Cl | H | OMe | 3.76 |
| 22 | Me | H | Cl | H | Br | 4.68 |

In yet another series of compounds useful as starting reagents in the present invention, substituents on both rings can be varied, via either of the above described methods. To illustrate compound preparation methods of this series, a three-necked flask fitted with a mechanical stirrer, reflux condenser and dropping funnel is filled with equimolar amounts of 2,6-dichloro-aniline (0.2 moles, 32.4 g) and o-nitrobenzene-sulfonyl chloride (0.2 moles, 44.2 g) Next, 40 cc pyridine is added to the reaction mixture dropwise, and the solution refluxed for two hours with the pyridine evaporated under vacuum. After solvent removal, the residue is titrated with slightly alkaline ice water to produce crude crystals. Pure white crystals of 2'-6'-dichloro-2-nitrobenzene-sulfonanilide are obtained upon crystallization from hot ethanol. Methylation is accomplished by mixing equimolar quantities of aryl-sulfonanilide and dimethylsulfate in a basic solution. Table 3 below lists some of the various compounds that can be prepared using this method.

TABLE 3

| Compound | R₁ | R₂ | R₃ | R₄ | R₅ | R₆ | R₇ | logP |
|---|---|---|---|---|---|---|---|---|
| 23 | —(CH₂)₃— | | Cl | H | NO₂ | H | H | 4.52 |
| 24 | —(CH₂)₃— | | Cl | H | NO₂ | H | Cl | 5.14 |
| 25 | —(CH₂)₃— | | OH | H | NO₂ | H | H | 3.52 |
| 26 | —(CH₂)₃— | | Me | H | NO₂ | H | H | 4.40 |
| 27 | —(CH₂)₃— | | Me | H | NO₂ | H | Cl | 5.01 |
| 28 | —(CH₂)₃— | | OH | H | H | H | H | 3.66 |
| 29 | —(CH₂)₃— | | OMe | H | NO₂ | H | H | 3.79 |
| 30 | —(CH₂)₃— | | Cl | H | H | H | H | 4.66 |
| 31 | Me | H | Me | H | NO₂ | H | H | 3.55 |
| 32 | Me | H | Me | H | H | NO₂ | H | 3.55 |
| 33 | Me | H | Me | H | H | H | NO₂ | 3.55 |
| 34 | Me | H | Cl | H | NO₂ | H | H | 3.70 |
| 35 | Me | H | Cl | H | H | NO₂ | H | 3.70 |
| 36 | Me | H | Cl | H | H | H | NO₂ | 3.70 |
| 37 | Me | H | OMe | H | NO₂ | H | H | 2.35 |
| 38 | Me | Cl | H | H | NO₂ | H | H | 3.70 |
| 39 | Me | Cl | H | H | H | H | NO₂ | 3.70 |
| 40 | Me | Cl | H | Cl | NO₂ | H | H | 4.31 |
| 41 | Me | Me | H | H | NO₂ | H | H | 3.55 |
| 42 | Me | Me | H | H | H | H | OMe | 3.62 |
| 43 | Me | OMe | H | H | NO₂ | H | H | 3.04 |
| 44 | Me | OMe | OMe | H | NO₂ | H | H | 3.00 |

Sulfone preparation in accordance with a preferred embodiment of the invention can be carried out as follows: the arylsulfonanilide is placed in an Erlenmyer flask and enough sulfuric acid (96% by weight) is added to make a 10% solution. The solution can be kept at room temperature, but if the reaction is too slow, it can be maintained, for example, at 95° C. in the oven. The dark acidic solution is next poured over ice with stirring and the bright colored precipitates of sulfone collected. The acidic filtrate is evaporated to lesser volume and neutralized with 10% sodium hydroxide, and the neutral solution extracted with ether. The liquid remaining, after evaporating off the ether, is the hydrolysis product, N'-methylaniline or its derivative. In a few instances extraction with ether is necessary as the amount of precipitate formed is minute. Ethanol and glacial acetic acid have been found to be preferred solvents for crystallization. Table 4 below lists the sulfones prepared by this method.

TABLE 4

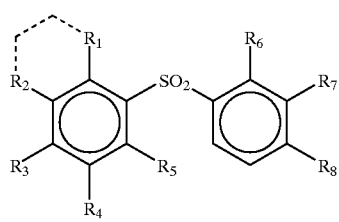

| Compound | R₁ | R₂ | R₃ | R₄ | R₅ | R₆ | R₇ | R₈ | logP |
|---|---|---|---|---|---|---|---|---|---|
| 45 | —NH(CH₂)₃— | | H | H | H | H | H | H | 3.06 |
| 46 | —NH(CH₂)₃— | | H | H | H | NO₂ | H | H | 2.95 |
| 47 | —NH(CH₂)₃— | | H | Cl | H | NO₂ | H | H | 3.56 |
| 48 | —NH(CH₂)₃— | | H | Cl | H | NO₂ | H | Cl | 4.18 |
| 49 | —NH(CH₂)₃— | | H | OH | H | NO₂ | H | H | 2.56 |
| 50 | —NH(CH₂)₃— | | H | Me | H | NO₂ | H | H | 3.42 |
| 51 | —NH(CH₂)₃— | | H | Me | H | NO₂ | H | Cl | 4.03 |
| 52 | —NH(CH₂)₃— | | H | Cl | H | H | H | H | 3.67 |
| 53 | —NH(CH₂)₃— | | H | OH | H | H | H | H | 2.67 |
| 54 | NHMe | H | H | H | H | H | H | H | 2.50 |
| 55 | NHMe | H | H | OMe | H | H | H | H | 2.46 |
| 56 | NHMe | H | H | Br | H | H | H | H | 3.37 |
| 57 | NHMe | H | H | Cl | H | H | H | H | 3.12 |
| 58 | NHMe | H | H | Me | H | H | H | H | 2.97 |
| 59 | H | Cl | NHMe | H | H | H | H | H | 3.12 |
| 60 | NHMe | Cl | H | H | H | H | H | H | 3.12 |
| 61 | NHMe | H | H | H | H | H | H | OMe | 2.46 |
| 62 | NHMe | H | H | H | H | H | H | Br | 3.37 |
| 63 | NHMe | H | H | H | H | H | H | Cl | 3.12 |
| 64 | NHMe | H | H | H | H | H | H | Me | 2.97 |
| 65 | H | H | NHMe | H | H | NO₂ | R | H | 2.39 |
| 66 | NHMe | H | H | H | H | NO₂ | H | H | 2.39 |

TABLE 4-continued

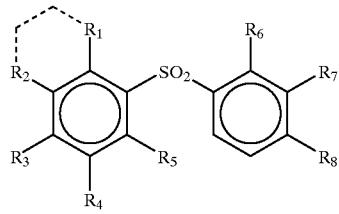

| Compound | R₁ | R₂ | R₃ | R₄ | R₅ | R₆ | R₇ | R₈ | logP |
|---|---|---|---|---|---|---|---|---|---|
| 67 | NHMe | H | H | H | H | H | NO₂ | H | 2.39 |
| 68 | NHMe | H | H | H | H | H | H | NO₂ | 2.39 |
| 69 | NHMe | H | H | Me | H | NO₂ | H | H | 2.86 |
| 70 | NHMe | H | H | Me | H | H | NO₂ | H | 2.86 |
| 71 | NHMe | H | H | Me | H | H | H | NO₂ | 2.86 |
| 72 | NHMe | H | H | Cl | H | NO₂ | H | H | 3.01 |
| 73 | NHMe | H | H | Cl | H | H | NO₂ | H | 3.01 |
| 74 | NHMe | H | H | Cl | H | H | H | NO₂ | 3.01 |
| 75 | NHMe | H | H | CH₃O | H | NO₂ | H | H | 2.35 |
| 76 | H | Cl | NHMe | Cl | H | NO₂ | H | H | 3.62 |
| 77 | H | Cl | NHMe | H | H | NO₂ | H | H | 3.01 |
| 78 | NHMe | Cl | H | H | H | NO₂ | H | H | 3.01 |
| 79 | H | Me | NHMe | H | H | NO₂ | H | H | 2.86 |
| 80 | NHMe | Me | H | H | H | NO₂ | H | H | 2.86 |
| 81 | NHEt | H | H | H | H | NO₂ | H | H | 2.98 |
| 82 | NHMe | H | H | H | H | Cl | H | H | 3.12 |
| 83 | NHMe | H | H | H | H | Br | H | H | 3.37 |
| 84 | NHMe | H | H | H | H | CF₃ | H | H | 3.49 |
| 85 | NHMe | H | H | Me | H | H | H | OMe | 2.93 |
| 86 | NHMe | H | H | H | H | OMe | H | Cl | 3.07 |
| 87 | NHMe | H | H | H | H | Cl | H | OMe | 3.07 |
| 88 | NHMe | H | H | H | H | Cl | H | Br | 3.98 |
| 89 | NHMe | H | H | OMe | H | NO₂ | H | H | 3.01 |

The following examples are preferred embodiments of the preparation of compounds in accordance with the present invention. It is to be understood, however, that these examples are for illustrative purposes only, and are not intended to limit the scope or spirit of the claims or the invention in any way.

EXAMPLE 1

6-(2'-NITROPHENYLSULFONYL)-1,3-DIMETHOXYBENZENE

To 25 g (0.18 moles) of m-dimethoxybenzene is added gradually with stirring 27 g (0.36 moles) of concentrated sulfuric acid. The temperature of the mixture is allowed to rise to 70° C. After standing for an hour, the viscous mixture is poured into a saturated solution of potassium carbonate. The white precipitate, which contains some carbonate and sulfate, is dried in an oven at 110°. To the powdered potassium salt is added 64 g (0.42 moles) of phosphorous oxychloride and the mixture is refluxed on a steam bath for an hour. The reaction mixture is then cooled to room temperature and poured over chipped ice with vigorous stirring. The white solid thus obtained is dissolved in ether, dried over anhydrous calcium chloride and the solvent removed at room temperature. The 2,4-dimethoxybenzene-sulfonyl chloride is crystallized from a 50:50 mixture of benzene and petroleum ether. The white crystals melt at 69–71° C. Anal. Calcd. for $C_8H_9ClO_4S$: C, 40.60; H, 3.80; Found: C, 39.59; H, 4.13.

Next, a mixture containing 35.8 g (0.15 moles) of 2,4-dimethoxy-benzenesulfonyl chloride and 56 g (0.45 moles) of sodium sulfite is shaken for 3 hours with 100 g of ice until complete solution is obtained. The solution is maintained alkaline by adding 5% sodium hydroxide (to prevent formation of sulfur dioxide) and kept cold by adding additional ice (higher temperatures may cause hydrolysis of the sulfonyl chloride). At the end of 3 hours unreacted 2,4-dimethoxybenzenesulfonyl chloride can be filtered off and the filtrate acidified with cold concentrated hydrochloric acid to yield a white crystalline precipitate of 2,4-dimethoxybenzenesulfinic acid, m.p. 89–91° C. (lit. 92° C.). The 2,4-demethoxybenzene-sulfinic acid is suspended in water and an equimolar quantity of sodium carbonate added in small portions to dissolve the sulfinic acid. The condensation of the sodium salt of the sulfinic acid with ortho-dinitrobenzene can be carried out by refluxing equimolar amounts of the two for 4 hours. Upon cooling the mixture is filtered and the solid residue recovered and crystallized using acetic acid to yield white shiny crystals of 2,4-dimethoxy-2'-nitrobiphenyl sulfone having a melting point of from about 157.5° C. to about 158.5° C.

EXAMPLE 2

2-(2-NITROPHENYLSULFONYL)-N-ETHYLANILINE

Freshly distilled N-ethylaniline (b.p. 204° C.) is prepared. To 3.43 g (0.0283 mole) of the N-ethylaniline is added 7.84 g (0.0372 mole) of 2-nitrobenzenesulfonyl chloride (98 w/w %). The mixture is stirred and becomes hot. Ten percent sodium hydroxide is added dropwise with stirring until the solution is slightly alkaline and N-ethyl-2-nitrobenzenesulfonanilide precipitated. The product is filtered and washed with water several times until the wash water is neutral to litmus paper. After the crude precipitate is dried at room temperature, it is purified by crystallizing from ethanol. N-ethyl-2-nitrobenzenesulfonanilide (2.26 g) is obtained (38% yield), with a melting point of 73.7–74.3° C. $^1$H NMR(deuterioacetone): δ 8–7.3 (m, 4 ArH), 6.9 (m, 5 ArH), 3.6 (q, 2H, N—CH$_2$), 1.1 (t, 3H, CH$_3$); ms:m/z 306 (M$^+$).

N-ethyl-2-nitrobenzenesulfonanilide thus obtained (2.26 g) is next placed in a beaker and enough sulfuric acid (98% by weight) is added to make a 10 w/w % solution. The solution is kept at 100° C. in an oven for one hour. The hot, dark-brown acid solution is then immediately poured on ice/water with stirring and the dark colored 2'-ethylamino-2-nitrodiphenyl sulfone is precipitated and washed with water until the wash water is neutral to litmus paper. The product is collected by filtration, and dissolved in hot ethanol and purified with activated charcoal. Crystallization from ethanol gives shiny yellow crystals of 2'-ethylamino-2-nitrodiphenyl sulfone (1.36 g, 60% yield), with a melting point of 114–115° C. $^1$H NMR (deuterioacetone): δ 7.5 (m, 1 ArH), 7.1 (m, 4 ArH), 6.8 (m, 1 ArH), 6.2 (m, 2ArH), 5.6 (broad s, 1H, NH), 2.9 (m, 2H, N—CH$_2$), 1.2 (t, 3H, CH$_3$); ms:m/z 306 (M$^+$) Anal. Calcd. for C$_{14}$H$_{14}$N$_2$O$_4$S: C, 54.90: H, 4.61. Found: C, 54.72; H, 4.76.

EXAMPLE 3

2-(2-BROMOPHENYLSULFONYL)-N-METHYLANILINE

Freshly distilled N-methylaniline (b.p. 196° C.) is prepared. To 1.07 g (0.01 mole) of the N-methylaniline is added 2.56 g (0.01 mole) of 2-bromobenzenesulfonyl chloride (98 w/w %). The mixture is stirred until hot. Ten percent sodium hydroxide is then added dropwise with stirring until the solution is slightly alkaline, and 2-bromo-N-methylbenzenesulfonanilide is formed as a viscous red-brown liquid. It is washed with water several times until the wash water is neutral to litmus paper. A viscous red-brown liquid is extracted with ether, and the ether layer is dried over magnesium sulfate, filtered and the solvent removed by evaporation. The yield of red-brown oil is 2.30 g (70% yield). $^1$H NMR (deuterioacetone): δ 7.1–8 (m, 9 ArH), 3.3 (s, 3H, N—CH$_3$).

2-bromo-N-methyl-benzenesulfonanilide (2.3 g is next placed in a beaker and enough sulfuric acid(98% by weight) is added to make a 10 w/w % solution. The solution is kept at 100° C. in an oven for one and one-half hours. The hot, dark brown acid solution is then poured on ice water with stirring and the dark colored 2-bromo-2'-methylaminodiphenyl sulfone is precipitated and washed with water until the wash water is neutral to litmus paper. The product is collected by filtration, and then dissolved in hot ethanol and purified with activated charcoal. Crystallization from ethanol gives crystals of 2-bromo-2'-methylaminodiphenyl sulfone (0.98 g, 43% yield), having a melting point of 136–137° C. $^1$H NMR (deuterioacetone): δ 7.9 (m, 1 ArH), 7.2 (m, 5 ArH), 6.3 (m, 2 ArH), 5.8 (broad s, 1H, NH), 2.6 (d, 3H, N—CH$_3$). Anal. calcd. for C$_{13}$H$_{12}$BrNO$_2$S: C, 47.90; H, 3.70; Br, 24.5. Found: C, 47.74; H, 3.63; Br, 24.63.

EXAMPLE 4

5 2-(2-CHLOROPHENYSULFONYL)-N-METHYLANILINE

To 0.97 g (~0.01 mole) of freshly prepared N-methylaniline (b.p. 196° C.) is added 1.94 g (~0.01 mole) of 2-chlorobenzenesulfonyl chloride (98 w/w %). The mixture is stirred until it becomes hot, and then ten percent sodium hydroxide is added dropwise with stirring until the solution is slightly alkaline. 2-chloro-N-methylbenzenesulfonanilide is formed as a viscous yellow liquid. It is washed with water several times until the wash water is neutral to litmus paper, and the viscous yellow liquid extracted with ether. The ether layer is dried over magnesium sulfate, filtered and the solvent removed by evaporation. The yield of a yellow oil is 2.2 g (87% yield).

The 2-chloro-N-methylbenzenesulfonanilide (2.2 g) is next placed in a beaker and enough sulfuric acid (98% by weight) added to make a 10 w/w % solution, which is kept at 100° C. in an oven for one hour. The hot, dark brown acid solution is then poured on ice/water with stirring and the dark colored, 2-chloro-2'-methylaminodiphenyl sulfone precipitated and washed with water until neutral and the product collected by filtration. The collected product is then dissolved in hot ethanol and purified with activated charcoal. Crystallization from ethanol provides white crystals of 2-chloro-2-methylaminodiphenyl sulfone (0.35 g, 16% yield), having a melting point of 154–155°. $^1$H NMR (deuterio-acetone): δ 7.8 (m, 1 ArH), 7.2 (m, 5 ArH), 6.3 (m, 2 ArH), 5.8 (broad s, 1H, NH), 2.6 (d, 3H, N—CH$_3$). Anal. calcd. for C$_{13}$H$_{12}$ClNO$_2$S: C, 55.40; H, 4.30; Cl, 12.60. Found: C, 55.24; H, 4.26; Cl, 12.28.

EXAMPLE 5

2-(2-TRIFLUOROMETHYLPHENYLSULFONYL)-N-METHYLNILINE

To 0.88 g (~0.01 mole) of freshly prepared N-methylaniline (b.p. 196° C.) is added 2.0 g (~0.01 mole) of 2-trifluoromethylbenzene-sulfonyl chloride (98 w/w %). The mixture is stirred until hot. Ten percent sodium hydroxide is then added dropwise with stirring until the solution is slightly alkaline. The 2-trifluoromethyl-N-methylbenzene-sulfonanilide is formed as a viscous light brown liquid. It is next washed with water several times until the wash water is neutral to litmus paper, and the viscous light brown liquid is extracted with ether. The ether layer is dried over magnesium sulfate, filtered and the solvent removed by evaporation. The yield of light brown oil is 2.5 g (96% yield). $^1$H NMR (deuterioacetone): δ 7.8.2 (m, 9 ArH), 3.2 (s, 3H, N—CH$_3$)

The 2-trifluoromethyl-N-methylbenzene sulfonanilide, (2.5 g) is then placed in a beaker and enough sulfuric acid (98% by weight) added to make a 10 w/w % solution. The solution is kept at 100° C. in an oven for two hours. The hot, dark brown acid solution is poured on ice/water with stirring and the dark colored 2'-methylamino-2- trifluoromethyldiphenyl sulfone is precipitated and is washed with water until the wash water is neutral to litmus paper. The product is collected by filtration and dissolved in hot ethanol and purified with activated charcoal. Crystallization from ethanol gives pale yellow to white crystals of 2'-methylamino-2-trifluoromethyldiphenyl sulfone (0.82 g, 33% yield), with a melting point of 95–96°. $^1$H NMR (deuterioacetone): δ 7.1–8.3 (m, 6 ArH), 6.7 (m, 2 ArH), 6.2 (broad s, 1H, NH), 2.8 (d, 3H, N—CH$_3$); ms:m/z 315 (M$^+$). Anal. calcd. for $C_{14}H_{12}F_3NO_2S$: C, 53.30; H, 3.80. Found: C, 53.13; H, 3.81.

EXAMPLE 6

2-(2-BROMOPHEYNYLSULFONYL)-3-CHLORO-N-METHYLANILINE

To 2.51 g (~0.017 mole) of freshly distilled 4-chloro-N-methylaniline (b.p. 102–103° C.) is added 4.26 g (~0.017 mole) of 2-bromo-benzenesulfonyl chloride (98 w/w %). The mixture is stirred until hot. Ten percent sodium hydroxide is added dropwise with stirring until the solution is slightly alkaline. The 2-bromo-4'-chloro-N-methylbenzene-sulfonanilide is formed as viscous liquid. It is washed with water several times until the wash water is neutral. The compound is dried overnight at room temperature. The yield is 4.2 g (69% yield). $^1$H NMR (deuterioacetone): δ 6.8–7.9 (m, 8 ArH), 3.2 (s, 3H, N—CH$_3$).

Next, the 2-bromo-4'-chloro-N-methylbanzene sulfonanilide, 2.20 g (0.006 mole) is placed in a beaker and enough sulfuric acid (98% by weight) is added to make a 10 w/w % solution. The solution is kept at 100° C. in an oven for one hour, and the hot, dark brown acid solution is then poured on ice/water with stirring and the dark colored 2-bromo-5'-chloro-2'-methylaminodiphenyl sulfone precipitated and washed with water until the wash water is neutral. The product is collected by filtration, and dissolved in hot ethanol and purified with activated charcoal. Crystallization from ethanol gives white crystals of 2-bromo-5'-chloro-2'-methyl-aminodiphenyl sulfone (1.3 g, 59% yield). The melting point is 142–143° C.

$^1$H NMR(deuterioacetone): δ 7.9 (m, 1 ArH), 7.4 (m, 4 ArH), 7.1 (d, 1 ArH), 6.4 (d, 1 ArH), 5.9 (broad s, 1H, NH), 2.7 (d, 3H, N—CH$_3$); ms:m/s 361 (M$^+$). Anal. calcd. for $C_{13}H_{11}BrClNO_2S$: C, 43.30; H, 3.10; N, 3.90. Found: C, 43.27; H, 3.03; N, 3.84.

EXAMPLE 7

2-(5-CHLORO-2-METHOXYPHENYLSULFONYL)-N-METHYLANILINE

Freshly distilled chlorosulfonic acid (b.p. 150° C.) 13.2 g (~0.1 mole) is placed in a 50 mL round-bottomed flask.

The liquid is cooled to 15° C. in an ice-water bath, and 27 mL of 4-chloroanisole (95 w/w %) is carefully added to chlorosulfonic acid. The mixture is stirred between additions and the temperature of the mixture is kept below 50° C. When the addition is complete, the mixture is refluxed on a steam bath for 2 hours. A homogeneous, viscous liquid is formed. The reaction mixture is then carefully poured into a 250 mL beaker of ice water. A white, solid mass of 5-chloro-2-methoxybenzenesulfonyl chloride is precipitated, filtered and dried (m.p. 88–89° C.). The 5-chloro-2-methoxybenzenesulfonyl chloride (15.7 g, ~0.07 mole) is added to 7.0 g (~0.07 mole) of N-methyl aniline by the procedure for making sulfonanilides as described previously. A light brown oil, 5-chloro-2-methoxy-N-methylbenzenesulfonanilide, (16 g, 80t yield) is obtained. $^1$H NMR (deuterioacetone): δ 6.3–7.9 (m, 8 ArH), 3.8 (s, 3H, OCH$_3$), 3.2 (s, 3H, N—CH$_3$); ms:m/z 311 (M$^+$).

The 5-chloro-2-methoxy-N-methylbenzenesulfonanilide, (7 g) is placed in a beaker and enough sulfuric acid (98% by weight) is added to make a 10 w/w % solution. The solution is kept at 100° C. in an oven for two hours, and the hot, dark brown acid solution then poured on ice/water with stirring and a dark solid mass of 5-chloro-2-methoxy-2'-methylaminodiphenyl sulfone is precipitated. The crude product is purified by using thin-layer chromatography (TLC) with methylene chloride as a solvent. A large blue band which fluoresced under short wavelength UV light is 5-chloro-2-methoxy-2'-methylaminodiphenyl sulfone. Using a Soxhlet apparatus, the product is extracted with methylene chloride overnight from silica gel. 5-chloro-2-methoxy-2'-methylaminodiphenyl sulfone (1 g, 14% yield) is obtained after removing the methylene chloride. The melting point is 158–159° C. $^1$H NMR (deuterioacetone): δ 6.5–7.8 (m, 5 ArH), 6.3 (m, 2 ArH), 3.5 (s, 3H, OCH$_3$, 2.7 (d, 3H, N—CH$_3$);ms:m/z 311 (M+). Anal. calcd. for $CQ_{14}H_{13}ClNO_2S$: C, 53.90; H, 4.50; Found: C, 53.58; H, 4.45.

EXAMPLE 8

2-(4-METHOXYPHENYLSULFONYL)-N,5-DIMETHYLANILINE

The synthetic procedure for this compound is the same as those procedures used to prepare the sulfonanilide compounds described hereinabove. The starting materials are 4-methoxybenzenesulfonyl chloride (6.12 g, 0.03 mole) and N-methyl-p-toluidine (3.5 g, 0.03 mole). The final product (4'-methyl-4-methoxy-N-methylbenzene-sulfonanilide (3.5 g, 42% yield) has a melting point of 78–79° C. $^1$H NMR (deuterioacetone): δ 7.1 (d, 2 ArH), 6.4–6.9 (m, 6 ArH), 3.7 (s, 3H, OCH$_3$), 2.9 (s, 3H, N—CH$_3$), 2.2 (s, 3H, CH$_3$).

The 4'-methyl-4-methoxy-N-methylbenzenesulfonanilide, (2.66 g, ~0.01 mole) is next dissolved in 24 mL of dry tetrahydrofuran (THF) under a nitrogen atmosphere and then 12 mL of 1.6 M. butyl lithium is rapidly added with stirring. The color of the mixture changes from yellow to dark brown when the reaction is initiated. After stirring overnight, water is added and the dark solid product is separated by vacuum filtration. The crude product is purified by using TLC with methylene chloride as a solvent. A large blue band which fluoresces under short wavelength UW light is 4-methoxy-2'-methylamino-5,'-methyldiphenyl sulfone. Using a Soxhlet apparatus, this product is extracted from silica gel with methylene chloride (98 w/w %) overnight and gives 0.58 g (22% yield) of 4-methoxy-2'-methylamino-5'-methyldiphenyl sulfone after stripping off the methylene chloride. The melting point is 164° C. $^1$H NMR (deuterioacetone): δ 7.9 (d, 2 ArH), 7.7 (s. 1 ArH), 7.3 (d, 1

ArH), 7 (d, 2 ArH), 6.6 (d, 1 ArH), 6.2 (broad s, 1H, NH), 3.8 (s, 3H, OCH$_3$), 2.8 (d, 3H, N—CH$_3$), 2.2 (s, 3H, CH$_3$); MS:m/z 291 (M$^+$). Anal. Calcd. for C$_{15}$H$_{17}$NO$_3$S: C, 61.80; H, 5.90. Found: C, 61.67; H, 5.86.

EXAMPLE 9

2-(4-METHOXYPHENYLSULFONYL)-5-CHLORO-N-METHYLANILINE

Freshly distilled 4-chloro-N-methylaniline (b.p. 102–103° C.) is prepared. To 2.83 g (0.02 mole) of 4-chloro-N-methylaniline is added 4.22 g (0.02 mole) of 4-methoxybenzenesulfonyl chloride (98 w/w %). The mixture is stirred until hot. Ten percent sodium hydroxide is added dropwise with stirring until the solution is slightly alkaline. 4'-chloro-4-methoxy-N-methylbenzenesulfonanilide is precipitated from the mixture and then filtered and washed with water several times until the wash water is neutral to litmus paper. After the crude precipitate is dried at room temperature, it is purified by crystallization from ethanol. Yield of the product 4'-chloro-4-methoxy-N-methylbenzenesulfonanilide is 5.7 g (91%). The melting point is 118–119° C. $^1$H NMR (deuterioacetone): δ 6.6–7.9 (m, 8 ArH), 3.7 (s, 3H, OCH$_3$), 3 (s, 3H, N—CH$_3$).

The thus obtained 4'-chloro-4-methoxy-N-methylbenzenesulfonanilide, (5.4 g) is next placed in a beaker and enough sulfuric acid (98% by weight) is added to make a 10 w/w % solution. The solution is kept at 100° C. in an oven for one hour. The hot, dark brown acid solution is then immediately poured on ice/water with stirring and the dark colored 5'-chloro-4-methoxy-2'-methylaminodiphenyl sulfone precipitated, filtered and washed with water until the wash water is neutral to litmus paper. This dark crude product is purified by using thin-layer chromatography (TLC) with methylene chloride as the solvent. The large blue band which fluoresced under UV light is identified as the 5'-chloro-4-methoxy-2'-methylaminodiphyenyl sulfone. Using a Soxhlet apparatus, the product is extracted overnight from the silica gel with methylene chloride. The 0.6 g (11% yield) of 5'-chloro-4-methoxy-2'-methylaminodiphenyl sulfone (green color) is obtained after removing the methylene chloride. The melting point is 141–142° C. $^1$H NMR (deuterioacetone): δ 7.4 (d, 2 ArH), 7.2 (m, 1 ArH), 6.8 (d, 1 ArH), 6.5 (d, 2 ArH), 6.2 (d, 1 ArH), 5.9 (broad s, 1H, NH), 3.6 (s, 3H, OCH$_3$), 2.7 (d, 3H, N—CH$_3$), MS:m/z 311(M$^+$). Anal. calcd. for C$_{14}$H$_{14}$BrClNO$_3$S: C, 53.90; H, 4.50; N, 4.50. Found: C, 53.40; H, 4.62; N, 4.15.

In accordance with another aspect of the present invention, it has been surprisingly and unexpectedly found that daryl sulfone compounds of the invention which possess an octanol/water partition coefficient (logP) of from about 2.5 to about 4, display enhanced anti-HIV efficacy. Without intending to limit the present invention to any particular theory, it is thought that a desired hydrophilic-lipophilic balance (logP) having preferred anti-HIV efficacy can be achieved by desired structures, providing for a desired structure-activity relationship.

The octanol/water partition coefficient (logP), as used in accordance with the present invention, can be calculated by any known method, an example of which is described in "Pallas with Prolog P Module", Compudrug NA, Rochester, N.Y., which is incorporated herein by reference.

EXAMPLE 10

Calculation of LOGP

An example of logP prediction by using a computer program (PrologP for Pallas) is shown below. This procedure provides three different calculations along with a weighted average.

TABLE 5

LOGP PREDICTION OF
2-(5-CHLORO-2-METHOXY-2-METHOXY-PHENYLSULFONYL)-N-METHYL-ANILINE:
RESULT WITH THE CDR DATABASE
Fragment database CDR

| OCCURRENCES | NAME OF CONTRIBUTOR | CONTRIBUTION VALUE |
|---|---|---|
| 2 | AR-CROSSCONJ.-ARI | 0.29 |
| 1 | AR-CROSSCONJ.-ARIV. | 0.29 |
| 7 | —CH— | 0.34 |
| 2 | —CH$_3$— | 0.70 |
| 1 | AL—O—AR | -0.45 |
| 1 | AR—CL | 0.92 |
| 1 | AR—NH—AL | -0.93 |
| 1 | AR-5O2-AR | -1.37 |
| 5 | C-ATOM | 0.16 | logP$_{CDR}$ = 3.58

TABLE 6

Fragment database ATOMIC

| OCCURRENCES | NAME OF CONTRIBUTOR | CONTRIBUTION VALUE |
|---|---|---|
| 2 | Cl | 0.63 |
| 5 | Cl44 | 0.09 |
| 7 | C44 | 0.31 |
| 1 | CL|C44 | 0.83 |
| 14 | H | 0.00 |
| 1 | N||CC44 | 0.50 |
| 1 | O||CC44 | -0.28 |
| 2 | O2Z | 0.34 |
| 1 | S||22C44C44ZZ | -1.59 | logP$_{Atomic}$ = 3.06

TABLE 7

Fragment database ATOMIC2

| OCCURRENCES | NAME OF CONTRIBUTOR | CONTRIBUTION VALUE |
|---|---|---|
| 2 | 005_C:CH3X | -1.08 |
| 7 | 024_C:R¦CH¦R | 0.01 |
| 5 | 026_C:R¦CX¦R | -0.10 |
| 13 | 047_H:C1(SP3), CO(SPS) | 0.33 |
| 1 | 050_H:H-HETERROATOM | -0.33 |
| 2 | 058_0: = 0 | 0.35 |
| 1 | 060_O:AL-0-AR, AR20 ,R% 0% R, R—O—C = X | 0.27 |
| 1 | 070_N:AR—NH—AL | 0.42 |
| 1 | 089_CL:CL-C1 (SP2) | 0.96 |
| 1 | 110_S:R—SO2—R | 0.37 | logP$_{Atomic2}$ = 2.71

The combined result: logP$_{combined}$=0.0301 logP$_{CDR}$+0.291 logP$_{ATOMIC}$+0.0408 logP$_{ATOMIC2}$3.07

ANTI-HIV DRUG TESTING SYSTEM

Compounds of the present invention were evaluated for anti-HIV efficacy by the National Cancer Institute's (NCI) In Vitro Anti AIDS Drug Discovery Program.

The NCI procedure is fully described, for example, in a bulletin provided by the *National Institutes of Health*, National Cancer Institute, Bethesda, Md. 20892, all of which is incorporated herein by reference. As related in the NCI bulletin, the procedure is based on O. W. Weislow et al., "New soluble-formazan assay for HIV-1 cytopathic effects: application to high flux screening of synthetic and natural products for AIDS-antiviral activity", *J. Natl. Cancer Inst.* 81:577–586 (1989), and is used to test for compounds active against human immunodeficiency virus (HIV), and is designed to detect compounds active at any stage of the virus reproductive cycle. As further related in the NCI bulletin, the assay includes killing of T4 lymphocytes by HIV. Amounts of HIV are added to cells, with a minimum of two cycles of virus reproduction found to be necessary to obtain the required cell killing. Compounds that interact with virions, cells, or virus gene-products to interfere with viral activities will protect cells from cytolysis. All were compared with a positive (e.g., AZT-treated) control evaluation at the same time under identical conditions. The procedure is set forth as follows:

A candidate compound is first dissolved in a suitable solvent, preferably dimethyl sulfoxide, then diluted 1:100 in cell culture medium before preparing serial half-$\log_{10}$ dilutions. T4 lymphocytes (CEM cell line) are then added and after a brief interval HIV-1 is added, resulting in a 1:200 final dilution of the compound. Uninfected cells with the compound serve as a toxicity control, and infected and uninfected without the compound serve as basic controls. Cultures are then incubated at 37° in a 5% carbon dioxide atmosphere for 6 days. The tetrazolium salt, XTT, is added to all wells, and cultures are incubated to allow formazan color development by viable cells. Individual wells are analyzed spectrophotometrically to quantitate formazan product, and in addition are viewed microscopically for detection of viable cells and confirmation of protective activity. Drug-treated virus-infected cells are compared with drug-treated noninfected cells and with other appropriate controls (untreated infected and untreated noninfected cells, drug-containing wells without cells, etc.) on the same plate. Data are reviewed in comparison with other tests performed at the same time and a determination as to activity is made.

Approximate values for 50% effective concentration ($EC_{50}$) against HIV cytopathic effects, 50% inhibitory concentration($IC_{50}$) for cell growth, and Therapeutic Index ($TI=(IC_{50}/EC_{50})$) have been calculated for each. Examples of compounds showing anti-HIV efficacy are provided below.

EXAMPLE 11

N-(2-nitrophenylsulfonyl)-2chloro-N-methylaniline

TABLE 8

| | Summary | Dose | Percent of | Percent of Control | |
|---|---|---|---|---|---|
| Index | Concentration | (Molar) | Protection | Infected | Uninfected |
| IC50 (Molar) | $3.41 \times 10^{-5}$ | $6.35 \times 10^{-8}$ | −0.27 | 4.74 | 100.87 |
| EC50 (Molar) | $4.38 \times 10^{-6}$ | $2.00 \times 10^{-7}$ | 2.73 | 7.25 | 99.33 |
| TI50 (IC/EC) | $7.79 \times 10^{0}$ | $6.34 \times 10^{-7}$ | −0.31 | 4.71 | 98.57 |
| | | $2.00 \times 10^{-6}$ | 10.40 | 14.88 | 98.15 |
| | | $6.33 \times 10^{-6}$ | 69.03 | 70.58 | 94.24 |
| | | $2.00 \times 10^{-5}$ | 61.87 | 63.78 | 75.70 |
| | | $6.32 \times 10^{-5}$ | −0.27 | 26.14 | 20.28 |
| | | $2.00 \times 10^{-4}$ | 2.73 | 28.44 | 3.62 |

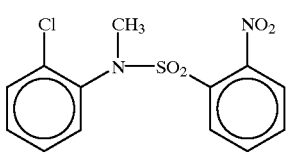

log P = 3.70
$EC_{50}$ mm = 9

EXAMPLE 12

N-(2-nitrophenylsulfonyl)-N,4-dimethylaniline

TABLE 9

| | Summary | Dose | Percent of | Percent of Control | |
|---|---|---|---|---|---|
| Index | Concentration | (Molar) | Protection | Infected | Uninfected |
| IC50 (Molar) | $3.88 \times 10^{-4}$ | $6.35 \times 10^{-8}$ | −3.51 | 1.67 | 92.92 |
| EC50 (Molar) | $1.25 \times 10^{-5}$ | $2.00 \times 10^{-7}$ | −1.72 | 3.37 | 95.84 |
| TI50 (IC/EC) | $31.0 \times 10^{0}$ | $6.34 \times 10^{-7}$ | −2.85 | 2.29 | 89.93 |
| | | $2.00 \times 10^{-6}$ | 9.89 | 14.40 | 84.10 |

TABLE 9-continued

| | Summary | Dose | Percent of | Percent of Control | |
|---|---|---|---|---|---|
| Index | Concentration | (Molar) | Protection | Infected | Uninfected |
| | 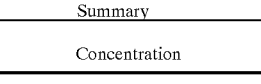 | $6.33 \times 10^{-6}$ | 21.98 | 91.09 | |
| | | $2.00 \times 10^{-5}$ | 73.56 | 84.35 | |
| | | $6.32 \times 10^{-5}$ | 18.44 | 24.65 | |
| | | $2.00 \times 10^{-4}$ | −0.58 | −0.75 | | log P = 3.55
EC$_{50}$ mm = 12

EXAMPLE 13

N-(3-nitrophenylsulfonyl)-N-methylaniline

TABLE 10

| | Summary | Dose | Percent of | Percent of Control | |
|---|---|---|---|---|---|
| Index | Concentration | (Molar) | Protection | Infected | Uninfected |
| IC50 (Molar) | $1.42 \times 10^4$ | $6.35 \times 10^{-8}$ | −11.07 | 3.37 | 94.85 |
| EC50 (Molar) | $4.25 \times 10^{-5}$ | $2.00 \times 10^{-7}$ | −10.87 | 3.54 | 93.23 |
| TI50 (IC/EC) | $3.34 \times 10^0$ | $6.34 \times 10^{-7}$ | −13.40 | 1.34 | 87.77 |
| | | $2.00 \times 10^{-6}$ | −6.93 | 6.97 | 87.19 |
| | | $6.33 \times 10^{-6}$ | −3.87 | 16.37 | 81.27 |
| | | $2.00 \times 10^{-5}$ | −3.74 | 9.75 | 83.82 |
| | | $6.33 \times 10^{-5}$ | 78.28 | 81.10 | 70.24 |
| | | $2.00 \times 10^{-4}$ | 5.28 | 17.59 | 41.45 | log P = 3.09
EC$_{50}$ mm = 20

EXAMPLE 14

8-(2-nitrophenylsulfonyl)6chloro-1,2,3,4-tetrahydroquinoline

TABLE 11

| | Summary | Dose | Percent of | Percent of Control | |
|---|---|---|---|---|---|
| Index | Concentration | (Molar) | Protection | Infected | Uninfected |
| IC50 (Molar) | $>2.00 \times 10^5$ | $6.35 \times 10^{-9}$ | 3.00 | 3.00 | 91.23 |
| EC50 (Molar) | $3.12 \times 10^{-7}$ | $2.00 \times 10^{-8}$ | 6.00 | 6.00 | 91.15 |
| TI50 (IC/EC) | $6.41 \times 10^{+1}$ | $6.34 \times 10^{-8}$ | 8.87 | 8.87 | 92.00 |
| | | $2.00 \times 10^{-7}$ | 25.31 | 25.31 | 87.12 |
| | | $6.33 \times 10^{-7}$ | 89.95 | 89.95 | 86.35 |
| | | $2.00 \times 10^{-6}$ | 88.75 | 88.75 | 92.60 |
| | | $6.32 \times 10^{-6}$ | 102.46 | 102.46 | 104.25 |
| | | $2.00 \times 10^{-5}$ | 86.18 | 86.18 | 96.12 | log P = 3.54
EC$_{50}$ mm = 0.3

EXAMPLE 15

8-(2-nitrophenylsulfonyl)6-methyl-1,2,3,4-tetrahydroquinoline

TABLE 12

| Summary | | Dose | Percent of | Percent of Control | |
|---|---|---|---|---|---|
| Index | Concentration | (Molar) | Protection | Infected | Uninfected |
| IC50 (Molar) | >2.00 × 10$^5$ | 6.35 × 10$^{-9}$ | −3.62 | 5.71 | 90.23 |
| EC50 (Molar) | 7.51 × 10$^{-8}$ | 2.00 × 10$^{-8}$ | −2.76 | 6.49 | 88.36 |
| TI50 (IC/EC) | >2.66 × 10$^{-2}$ | 6.34 × 10$^{-8}$ | 44.07 | 49.10 | 90.52 |
| | | 2.00 × 10$^{-7}$ | 86.34 | 87.57 | 87.08 |
| | | 6.33 × 10$^{-7}$ | 84.23 | 85.65 | 89.34 |
| | | 2.00 × 10$^{-6}$ | 106.84 | 106.22 | 91.01 |
| | | 6.32 × 10$^{-6}$ | 109.26 | 108.43 | 91.21 |
| | | 2.00 × 10$^{-5}$ | 97.37 | 97.61 | 100.66 |

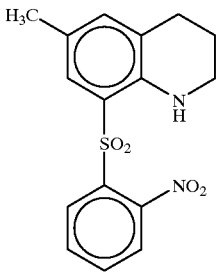

log P = 3.42
EC$_{50}$ mm = 0.5

EXAMPLE 16

8-(2-nitrophenylsulfonyl)-1,2,3,4-tetrahydroquinoline

TABLE 13

| Summary | | Dose | Percent of | Percent of Control | |
|---|---|---|---|---|---|
| Index | Concentration | (Molar) | Protection | Infected | Uninfected |
| IC50 (Molar) | 4.99 × 10$^{-5}$ | 6.35 × 10$^{-8}$ | −1.64 | 0.39 | 98.88 |
| EC50 (Molar) | 1.32 × 10$^{-6}$ | 2.00 × 10$^{-7}$ | 6.11 | 7.99 | 98.88 |
| TI50 (IC/EC) | 3.78 × 10$^{+1}$ | 6.34 × 10$^{-7}$ | 16.27 | 17.94 | 100.36 |
| | | 2.00 × 10$^{-6}$ | 69.39 | 70.00 | 95.43 |
| | | 6.33 × 10$^{-6}$ | 89.10 | 89.32 | 94.05 |
| | | 2.00 × 10$^{-5}$ | 76.38 | 76.85 | 95.83 |
| | | 6.32 × 10$^{-5}$ | 33.62 | 34.95 | 38.15 |
| | | 2.00 × 10$^{-4}$ | −0.28 | 1.73 | 1.77 |

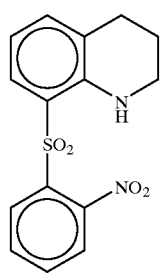

log P = 2.95
EC$_{50}$ mm = 3

EXAMPLE 17

8-(phenylsulfonyl)-1,2,3,4-tetrahydroquinoline

TABLE 14

| Summary | | Dose | Percent of | Percent of Control | |
|---|---|---|---|---|---|
| Index | Concentration | (Molar) | Protection | Infected | Uninfected |
| IC50 (Molar) | >2.00 × 10$^{-45}$ | 6.35 × 10$^{-8}$ | −1.54 | 0.49 | 87.15 |
| EC50 (Molar) | 1.40 × 10$^{-5}$ | 2.00 × 10$^{-7}$ | 0.38 | 2.37 | 84.19 |
| TI50 (IC/EC) | 1.43 × 10$^{+1}$ | 6.34 × 10$^{-7}$ | 0.22 | 2.22 | 89.71 |
| | | 2.00 × 10$^{-6}$ | 2.49 | 4.44 | 93.26 |
| | | 6.33 × 10$^{-6}$ | 13.35 | 15.08 | 94.35 |
| | | 2.00 × 10$^{-5}$ | 67.02 | 67.68 | 101.05 |
| | | 6.32 × 10$^{-5}$ | 59.78 | 60.58 | 74.24 |
| | | 2.00 × 10$^{-4}$ | 42.17 | 43.33 | 62.11 |

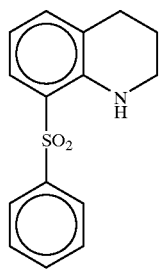

log P = 3.06
EC$_{50}$ mm = 20

EXAMPLE 18

2-(2-nitrophenylsulfonyl)4-chloro-N-methylaniline

TABLE 15

| Summary | | Dose | Percent of | Percent of Control | |
|---|---|---|---|---|---|
| Index | Concentration | (Molar) | Protection | Infected | Uninfected |
| IC50 (Molar) | >2.00 × 10$^{-4}$ | 6.35 × 10$^{-8}$ | 46.06 | 47.14 | 99.00 |
| EC50 (Molar) | 7.50 × 10$^{-8}$ | 2.00 × 10$^{-7}$ | 75.99 | 76.47 | 102.32 |
| TI50 (IC/EC) | >2.67 × 10$^{+3}$ | 6.34 × 10$^{-7}$ | 102.43 | 102.38 | 101.13 |
| | | 2.00 × 10$^{-6}$ | 93.43 | 93.56 | 95.81 |
| | | 6.33 × 10$^{-6}$ | 93.26 | 93.39 | 100.90 |
| | | 2.00 × 10$^{-5}$ | 83.96 | 84.27 | 93.56 |
| | | 6.32 × 10$^{-5}$ | 85.47 | 85.76 | 96.99 |
| | | 2.00 × 10$^{-4}$ | 74.00 | 74.52 | 83.98 |

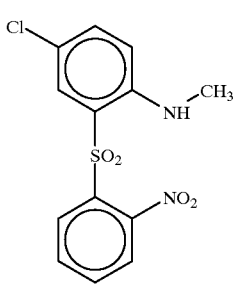

log P = 3.01
EC$_{50}$ mm = 0.08

EXAMPLE 19

4-(2-nitrophenylsulfonyl)-2-chloro-N-methylaniline

TABLE 16

| Summary | | Dose | Percent of | Percent of Control | |
|---|---|---|---|---|---|
| Index | Concentration | (Molar) | Protection | Infected | Uninfected |
| IC50 (Molar) | >2.00 × 10$^{-4}$ | 6.35 × 10$^{-8}$ | 12.33 | 16.71 | 111.39 |
| EC50 (Molar) | 1.19 × 10$^{-7}$ | 2.00 × 10$^{-7}$ | 81.98 | 82.88 | 105.99 |
| TI50 (IC/EC) | >1.69 × 10$^{+3}$ | 6.34 × 10$^{-7}$ | 89.78 | 90.29 | 106.63 |
| | | 2.00 × 10$^{-6}$ | 100.46 | 100.44 | 109.80 |
| | | 6.33 × 10$^{-6}$ | 99.52 | 99.54 | 99.96 |
| | | 2.00 × 10$^{-5}$ | 96.67 | 96.84 | 89.70 |
| | | 6.32 × 10$^{-5}$ | 106.20 | 105.89 | 95.20 |
| | | 2.00 × 10$^{-4}$ | 100.35 | 100.33 | 111.28 |

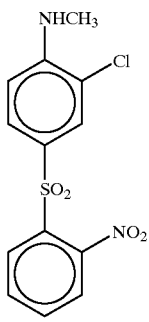

log P = 3.01
EC$_{50}$ mm = 0.1

EXAMPLE 20

4-(2-nitrophenyisulfonyl)-N,2-dimethylaniline

TABLE 17

| Summary | | Dose | Percent of | Percent of Control | |
|---|---|---|---|---|---|
| Index | Concentration | (Molar) | Protection | Infected | Uninfected |
| IC50 (Molar) | 3.27 × 10$^{-5}$ | 6.35 × 10$^{-8}$ | 7.87 | 12.48 | 107.48 |
| EC50 (Molar) | 1.83 × 10$^{-7}$ | 2.00 × 10$^{-7}$ | 53.86 | 56.17 | 97.11 |
| TI50 (IC/EC) | 1.79 × 10$^{-2}$ | 6.34 × 10$^{-7}$ | 65.00 | 66.75 | 92.98 |
| | | 2.00 × 10$^{-6}$ | 97.01 | 97.16 | 94.04 |
| | | 6.33 × 10$^{-6}$ | 102.75 | 102.61 | 98.17 |
| | | 2.00 × 10$^{-5}$ | 78.58 | 79.65 | 76.90 |
| | | 6.32 × 10$^{-5}$ | 10.11 | 14.60 | 13.86 |
| | | 2.00 × 10$^{-4}$ | 10.72 | 15.18 | 11.95 |

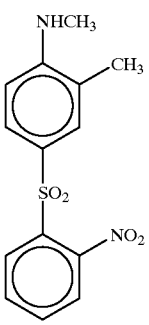

log P = 2.86
EC$_{50}$ mm = 0.2

EXAMPLE 21

2-(2-nitrophenylsulfonyl)-N-methylaniline

TABLE 18

| Summary | | Dose | Percent of | Percent of Control | |
|---|---|---|---|---|---|
| Index | Concentration | (Molar) | Protection | Infected | Uninfected |
| IC50 (Molar) | $4.35 \times 10^5$ | $6.35 \times 10^{-8}$ | 2.40 | 12.16 | 98.53 |
| EC50 (Molar) | $1.02 \times 10^{-6}$ | $2.00 \times 10^{-7}$ | 4.77 | 14.29 | 104.87 |
| TI50 (IC/EC) | $4.24 \times 10^{+1}$ | $6.34 \times 10^{-7}$ | 19.34 | 27.41 | 99.44 |
| | | $2.00 \times 10^{-6}$ | 93.06 | 93.75 | 101.25 |
| | | $6.33 \times 10^{-6}$ | 106.84 | 106.16 | 109.40 |
| | | $2.00 \times 10^{-5}$ | 98.73 | 98.86 | 104.09 |
| | | $6.32 \times 10^{-5}$ | 24.17 | 31.75 | 23.92 |
| | | $2.00 \times 10^{-4}$ | −15.92 | −4.33 | −4.40 |

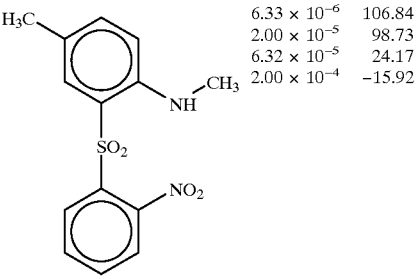

log P = 2.86
$EC_{50}$ mm = 0.4

EXAMPLE 22

2-(2-nitrophenylsulfonyl)-N-methylaniline

TABLE 19

| Summary | | Dose | Percent of | Percent of Control | |
|---|---|---|---|---|---|
| Index | Concentration | (Molar) | Protection | Infected | Uninfected |
| IC50 (Molar) | $1.48 \times 10^{-5}$ | $6.35 \times 10^{-8}$ | 88.20 | 88.79 | 96.33 |
| EC50 (Molar) | | $2.00 \times 10^{-7}$ | 99.97 | 99.97 | 92.07 |
| TI50 (IC/EC) | $1.80 \times 10^{+2}$ | $6.34 \times 10^{-7}$ | 110.93 | 110.38 | 97.06 |
| | | $2.00 \times 10^{-6}$ | 107.69 | 107.31 | 88.74 |
| | | $6.33 \times 10^{-6}$ | 100.68 | 100.65 | 87.28 |
| | | $2.00 \times 10^{-5}$ | 40.52 | 43.49 | 36.62 |
| | | $6.32 \times 10^{-5}$ | 0.71 | 5.67 | 15.40 |
| | | $2.00 \times 10^{-4}$ | 1.42 | 6.35 | 1.98 |

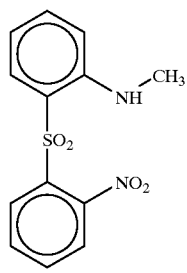

log P = 2.39
$EC_{50}$ mm = 1

EXAMPLE 23

2-nitrophenylsulfonyl)-N-ethylaniline

TABLE 20

| Summary | | Dose | Percent of | Percent of Control | |
|---|---|---|---|---|---|
| Index | Concentration | (Molar) | Protection | Infected | Uninfected |
| IC50 (Molar) | $3.22 \times 10^{-5}$ | $6.35 \times 10^{-8}$ | 5.99 | 36.07 | 93.68 |
| EC50 (Molar) | $2.32 \times 10^{-6}$ | $2.00 \times 10^{-7}$ | 1.50 | 33.02 | 70.72 |
| TI50 (IC/EC) | $1.39 \times 10^{+1}$ | $6.34 \times 10^{-7}$ | 31.28 | 53.27 | 89.42 |
| | | $2.00 \times 10^{-6}$ | 46.07 | 63.33 | 89.00 |
| | | $6.33 \times 10^{-6}$ | 81.37 | 87.33 | 83.07 |
| | | $2.00 \times 10^{-5}$ | 53.62 | 68.46 | 68.63 |
| | | $6.32 \times 10^{-5}$ | −14.96 | 21.83 | 23.63 |
| | | $2.00 \times 10^{-4}$ | 17.22 | 43.71 | 13.69 |

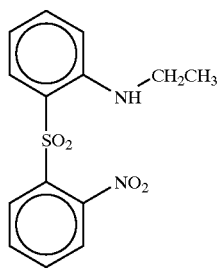

log P = 2.98
$EC_{50}$ mm = 2.5

EXAMPLE 24

2-(2-nitrophenylsulfonyl)-6-chloro-N-methylaniline

TABLE 21

| Summary | | Dose | Percent of | Percent of Control | |
|---|---|---|---|---|---|
| Index | Concentration | (Molar) | Protection | Infected | Uninfected |
| IC50 (Molar) | $>2.00 \times 10^{-5}$ | $6.35 \times 10^{-9}$ | 2.69 | 4.64 | 88.49 |
| EC50 (Molar) | $2.20 \times 10^{-7}$ | $2.00 \times 10^{-8}$ | 8.88 | 10.70 | 92.23 |
| TI50 (IC/EC) | $>9.08 \times 10^{+1}$ | $6.34 \times 10^{-8}$ | 12.15 | 13.91 | 87.44 |
| | | $2.00 \times 10^{-7}$ | 45.89 | 46.97 | 85.20 |
| | | $6.33 \times 10^{-7}$ | 100.04 | 100.04 | 86.39 |
| | | $2.00 \times 10^{-6}$ | 93.94 | 94.06 | 85.64 |
| | | $6.32 \times 10^{-6}$ | 95.96 | 96.04 | 91.48 |
| | | $2.00 \times 10^{-5}$ | 89.55 | 89.76 | 85.50 |

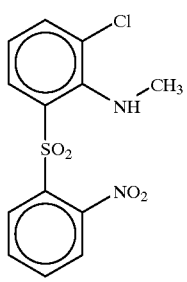

log P = 3.01
$EC_{50}$ mm = 4

EXAMPLE 25

2-phenylsulfonyl-4-chloro-N-methylaniline

TABLE 22

| Summary | | Dose | Percent of | Percent of Control | |
|---|---|---|---|---|---|
| Index | Concentration | (Molar) | Protection | Infected | Uninfected |
| IC50 (Molar) | >2.00 × $10^{-4}$ | 6.35 × $10^{-8}$ | −1.32 | 5.77 | 91.87 |
| EC50 (Molar) | 9.84 × $10^{-6}$ | 2.00 × $10^{-7}$ | 0.57 | 7.53 | 92.05 |
| TI50 (IC/EC) | >2.03 × $10^{-1}$ | 6.34 × $10^{-7}$ | −1.18 | 5.90 | 86.41 |
| | | 2.00 × $10^{-6}$ | 2.94 | 9.73 | 91.52 |
| | | 6.33 × $10^{-6}$ | 22.92 | 28.32 | 89.58 |
| | | 2.00 × $10^{-5}$ | 93.96 | 94.38 | 87.21 |
| | | 6.32 × $10^{-5}$ | 91.92 | 92.49 | 97.16 |
| | | 2.00 × $10^{-4}$ | 22.02 | 27.48 | 75.93 |

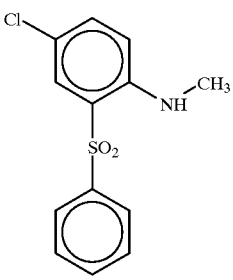

log P = 3.12
$EC_{50}$ mm = 6

EXAMPLE 26

2-chlorophenylsulfonyl)-N-methylaniline

TABLE 23

| Summary | | Dose | Percent of | Percent of Control | |
|---|---|---|---|---|---|
| Index | Concentration | (Molar) | Protection | Infected | Uninfected |
| IC50 (Molar) | 1.46 × $10^{-4}$ | 6.35 × $10^{-8}$ | 23.72 | 48.13 | 93.18 |
| EC50 (Molar) | 2.97 × $10^{-5}$ | 2.00 × $10^{-7}$ | −22.63 | 16.61 | 60.78 |
| TI50 (IC/EC) | 4.93 × $10^{0}$ | 6.34 × $10^{-7}$ | −8.87 | 25.97 | 96.10 |
| | | 2.00 × $10^{-6}$ | −5.07 | 28.55 | 91.25 |
| | | 6.33 × $10^{-6}$ | 24.46 | 48.63 | 84.16 |
| | | 2.00 × $10^{-5}$ | 41.40 | 60.15 | 78.15 |
| | | 6.32 × $10^{-5}$ | 68.10 | 78.31 | 93.26 |
| | | 2.00 × $10^{-4}$ | 3.76 | 34.56 | 33.90 |

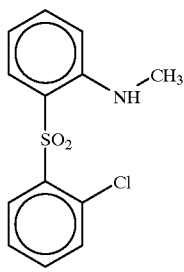

log P = 3.12
$EC_{50}$ mm = 20

EXAMPLE 27

2-(4-chloro-2-methoxyphenylsulfonyl)-N-methylaniline

TABLE 24

| Summary | | Dose | Percent of | Percent of Control | |
|---|---|---|---|---|---|
| Index | Concentration | (Molar) | Protection | Infected | Uninfected |
| IC50 (Molar) | >2.00 × 10$^{-4}$ | 6.35 × 10$^{-8}$ | 0.03 | 2.03 | 95.79 |
| EC50 (Molar) | 1.06 × 10$^{-4}$ | 2.00 × 10$^{-7}$ | 1.18 | 3.16 | 91.65 |
| TI50 (IC/EC) | >1.88 × 10$^{0}$ | 6.34 × 10$^{-7}$ | 1.22 | 3.20 | 97.11 |
| | | 2.00 × 10$^{-6}$ | 0.36 | 2.35 | 96.55 |
| | | 6.33 × 10$^{-6}$ | 1.52 | 3.49 | 94.76 |
| | | 2.00 × 10$^{-5}$ | 5.32 | 7.21 | 88.35 |
| | | 6.32 × 10$^{-5}$ | 27.08 | 28.54 | 95.89 |
| | | 2.00 × 10$^{-4}$ | 78.80 | 79.22 | 83.92 |

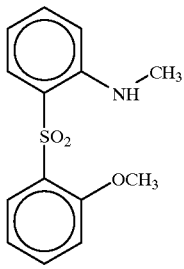

log P = 3.07
EC$_{50}$ mm = 106

What is claimed is:

1. A method of treating human immunodeficiency virus infection which comprises administering to a human in need thereof an effective amount of a compound of the formula selected from the group consisting of

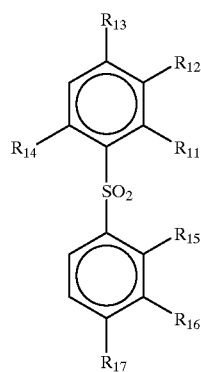
(III)

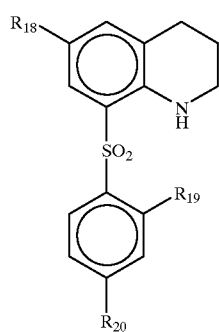
(IV)

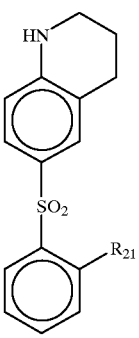
(V)

wherein $R_{11}$ is hydrogen, $C_1$–$C_4$ amine, with the proviso that when $R_{11}$ is H, $R_{13}$ is $C_1$–$C_4$ amine; $R_{12}$ is hydrogen, $C_1$–$C_4$ alkyl or halogen; $R_{13}$ is hydrogen, $C_1$–$C_4$ amine, with the proviso that when $R_{13}$ is H, $R_{11}$ is $C_1$–$C_4$ amine; $R_{14}$ is hydrogen or halogen; $R_{15}$ is nitro; $R_{16}$ is hydrogen or nitro; $R_{17}$ is hydrogen, $C_1$–$C_4$ alkyl, $C_1$–$C_4$ alkoxy, nitro or halogen; $R_{18}$ is hydrogen, $C_1$–$C_4$ alkoxy, hydroxy, or halogen; $R_{19}$ is nitro; $R_{20}$ is hydrogen or halogen; and $R_{21}$ is $NO_2$; and pharmaceutically acceptable salts thereof.

2. The method of claim 1 wherein said compound has an octanol/water partition coefficient (LogP) of from about 2.5 to about 4.

3. The method of claim 2 wherein said compound is administered in a pharmaceutical formulation which comprises said compound or a pharmaceutically acceptable salt thereof associated with one or more pharmaceutically acceptable carriers, excipients or diluents therefor.

* * * * *